United States Patent
Delrieu et al.

[19]

[11] Patent Number: 5,961,990
[45] Date of Patent: Oct. 5, 1999

[54] COSMETIC PARTICULATE GEL DELIVERY SYSTEM AND METHOD OF PREPARING COMPLEX GEL PARTICLES

[75] Inventors: Pascal Delrieu; Li Ding, both of Castanet Tolosan, France

[73] Assignee: Kobo products s.a.r.l., France

[21] Appl. No.: 08/850,167

[22] Filed: May 2, 1997

[51] Int. Cl.[6] ..................................................... A61K 9/14
[52] U.S. Cl. ..................... 424/401; 424/484; 424/485; 424/489; 424/60; 424/70.1; 424/70.9; 424/70.28; 424/78.03; 514/937; 514/944
[58] Field of Search ..................................... 424/401, 484, 424/485, 489, 60, 70.1, 70.9, 70.28, 78.03; 514/937, 944

[56] References Cited

U.S. PATENT DOCUMENTS

| | | |
|---|---|---|
| 4,465,693 | 8/1984 | Strauss et al. . |
| 4,847,076 | 7/1989 | Deshpande et al. . |
| 4,970,067 | 11/1990 | Panandiker et al. . |
| 4,994,273 | 2/1991 | Zentner . |
| 5,077,211 | 12/1991 | Yarosh . |
| 5,135,748 | 8/1992 | Ziegler et al. . |
| 5,151,264 | 9/1992 | Samain et al. . |
| 5,169,624 | 12/1992 | Ziegler et al. . |
| 5,171,526 | 12/1992 | Wong et al. . |
| 5,288,484 | 2/1994 | Tashjian . |
| 5,302,389 | 4/1994 | Kripke et al. . |
| 5,314,915 | 5/1994 | Rencher . |
| 5,352,458 | 10/1994 | Yarosh . |
| 5,417,982 | 5/1995 | Modi . |
| 5,449,519 | 9/1995 | Wolf et al. . |
| 5,457,093 | 10/1995 | Cini . |
| 5,494,533 | 2/1996 | Woodin, Jr. et al. . |
| 5,496,852 | 3/1996 | Oliver . |
| 5,534,247 | 7/1996 | Franjac et al. . |

FOREIGN PATENT DOCUMENTS

| | | |
|---|---|---|
| 470872 | 2/1992 | European Pat. Off. . |
| 96/29080 | 9/1996 | WIPO . |

OTHER PUBLICATIONS

Crodacel Q Range, Product Sheet, Croda Chemicals Ltd., Jul. 1989.

*Primary Examiner*—Raj Bawa
*Attorney, Agent, or Firm*—Handal and Morofsky

[57] ABSTRACT

A protective cosmetic particulate gel delivery system for a topically applied active agent employs an agar gel and a restraining polymer to retain the actve agent in the gel. The particles have an average particle diameter of at least 0.05 mm while the restraining polymer has a molecular weight of at least 50,000 daltons and has retention groups to bind the active agent. The restraining polymers can be selected from the group consisting of polyquaternium 24, laurdimonium hydroxyethylcellulose, cocodimonium hydroxyethylcellulose, steardimonium hydroxyethylcellulose, quaternary ammonium substituted water-soluble polysaccharides, alleyl quaternary celluloses and polypeptides having or provided with retention groups to retain the active agent. The gel particles of the invention are manually crushable on the skin to increase the surface area of the gel particle material and expose the restraining polymer to the skin or other body surface for release of the active agent. The delivery system can be incorporated in multiphase cosmetic formulations such as gels, creams and lotions.

14 Claims, 2 Drawing Sheets

PRIOR ART

COSMETIC PARTICULATE GEL DELIVERY SYSTEM AND METHOD OF PREPARING COMPLEX GEL PARTICLES

BACKGROUND OF THE INVENTION

1. Field of the Invention

This invention relates to a novel cosmetic or dermatological delivery system having a variety of applications for delivery of topically applied active agents to the skin, to methods of preparing such delivery systems and to cosmetic or dermatological formulations in which the delivery systems may be incorporated. Of particular interest are multiphase cosmetic formulations such as gels, creams and lotions.

One difficulty with known cosmetic delivery systems is that of protecting labile compounds from reacting prematurely. Furthermore, certain biologically active substances, e.g. alphahydroxy acids, are known to benefit the skin by improving skin softness and appearance. However, many such actives tend to cause irritation because they have the capacity, if the local concentration is too high, to penetrate deeply through the stratum corneum to more sensitive living tissue. Accordingly, there is a need for a delivery system that can separate active agents from a formulating excipient or adjuvant and provide controlled release of the active substances at the point of application. It would also be advantageous to provide a delivery system for actives that permits localized concentration of actives at the point of delivery, for instance, at the skin's surface.

One approach is for actives to be bound to carrier molecules to provide a complex which will remain stable in cosmetic preparations. When the complex is applied to the skin, the active is released or dissociated from the delivery system and is absorbed into the skin to provide the desired effect. Such systems are known to the art, but they fail adequately to separate the actives from formulation ingredients. Nor do they provide a means for concentrating delivery of actives at a desired location, for example the skin's surface. Another problem encountered in delivering actives to the skin is that they may react undesirably with the delivery system itself. Cosmetic actives can be stabilized in suspensions and formulas as cosmetic preparations. However, formulating the thus stabilized actives requires elevated temperatures and varying pH levels which may modify the active and cause stability problems with the formulation.

Polyphenols such as procyanidin oligomers, are good examples of labile actives that are known to polymerize undesirably in reaction with common components of many cosmetic formulations. Polyphenols include catechins which are botanically derived antioxidant polyphenols extracted from grapeseed, green tea and other woody plants. Catechins are useful for free radical scavenging in anti-ageing formulations to protect against the effects of ultraviolet light.

A multilayer particulate delivery systems for these and other active ingredients, and for controlled systemic release of drugs, is taught by Samain et al. in the U.S. Pat. No. 5,151,264. Samain et al. disclose what they describe as "biomimetic" carriers comprising an absorbent, solid, core of modified starch and an outer phospholipid coating which mimics a typical cellular membrane to avoid triggering the body's defenses to the incursion of foreign particles. Though Samain et al.'s multi-layer particles are very effective for many applications, it would be desirable to have a delivery system that provides additional options for release of the active at the delivery point or zone, and which permits quicker release at the skin's surface than is possible from Samain's dimensionally stable solid core particles.

Delivery systems for active substances having biologic or cosmetic activity, "actives" herein, can be either sustained release or controlled release systems. Sustained release systems release the active continuously from the moment of formulation. The active to be delivered is embedded within a matrix whose diffusion coefficient is low (lower than water for instance) so that the active slowly releases out of the matrix. This type of continuous release system is not suitable for cosmetic formulations because constant release of the active upon formulation of the system, for example into a cosmetic cream, creates instability affecting shelf life and effectiveness. In contrast, controlled release systems release the active when initiated by a particular event. The active is chemically or physically bound to a matrix in the controlled release system and is subsequently released when that bond is destroyed by an external event. For example, with the Samain et al. multilayer particles, the active ingredient is linked to the particle by means of ionic bonding. The release of the active is initiated by encounter with skin moisture, which has a relatively low ionic strength.

Gel forming polymers provide a delivery system by forming a matrix in which active substances can be entrapped. An example of a gel forming polymer is agar, also known as "agar-agar", a polysaccharide commonly used as a medium for electrophoresis and chromatography. It is known that agar can be formed into beads of various sizes for delivery of actives such as pharmaceutical drugs or even biological cells. A problem with agar beads is they form a sustained release system which, as described above, is not suitable for cosmetic applications because release of the actives commences at formulation.

2. Description of Related Art Including Information Disclosed Under 37 CFR 1.97 and 37 CFR 1.98

Cini et al U.S. Pat. No. 5,457,093 discloses a sustained release gel formulation for delivering growth factors to wound sites, especially ophthalmic wounds. Various polysaccharide gels are used, including agar. Cini's gels are not intended for formulation into cosmetics and would presumably dissolve or disperse and fail to protect their actives, if subjected to mixing with an aqueous phase cosmetic vehicle. The actives are continuously released from the gel from the moment the gel is incorporated into a cosmetic formulation containing an aqueous phase. Accordingly, Cini's gel formulations cannot be used in cosmetic emulsions that are required to have significant shelf lives.

Modi U.S. Pat. No. 5,417,982 discloses a controlled release delivery system where a polymer-gel matrix comprised of two water-soluble polymers is incorporated into microspheres. Biodegradation of the microsphere matrix provides a controlled release oral or injection delivery system for administering therapeutic doses of proteins or polypeptides internally or systemically. Modi's system is apparently not intended for, and would not be suitable for, topical delivery and release of actives.

Rencher U.S. Pat. No. 5,314,915 provides a local anesthetic delivery system comprising a polymer blend of sodium carboxymethyl cellulose and xanthan gum or sodium alginate. Rencher's formulation is a continuous phase adhesive or teething gel, rather than being particulate, and does not provide a delivery system that will facilitate the incorporation of actives in a cosmetic or pharmaceutical formulation with good separation of the active from the formulation. Rencher's continuous phase system does not protect any adsorbed actives if incorporated into a cosmetic cream or lotion containing an aqueous phase.

Yarosh U.S. Pat. No. 5,077,211 discloses delivery of DNA repair enzymes in active form to living mammalian cells in situ by incorporating purified enzymes into liposomes which are diluted into media and added to target cells. The DNA enzymes are reportedly active topically and elsewhere to correct cellular deficiencies, stimulating generation of healthy tissue to replace aged or damaged skin. Yarosh's liposomes are prepared by rehydrating lipid mixture films with a concentrated, buffered, aqueous solution of the enzyme, agitating, sonicating and separating out the desired liposome spheres. Lipid mixtures used are based upon phosphatidyl choline (lecithin) as a primary ingredient, with dicetyl phosphate or stearylamine as secondary ingredients and with cholesterol an optional tertiary ingredient, see Examples 3 and 4.

According to Yarosh, the liposomes are incorporated into polyglycol gels, apparently at room temperature, for topical application, apparently under laboratory conditions. Consideration of Yarosh's delivery vehicles suggests that while they may be adequate for laboratory testing, they would not be suitable for commercial applications.

Yarosh U.S. Pat. No. 5,352,458 and Kripke et al. U.S. Pat. No. 5,302,389 disclose the use of Yarosh's DNA repair enzymes, prepared according to Yarosh '211, respectively for enhancing tanning by stimulating enhanced melanin production, and for suppressing UV-induced T-cell immune response and thence the associated redness, tenderness and inflammation.

Clearly, significant benefits might be obtained from a cosmetic or pharmaceutical formulation having a carrier to deliver such DNA repair, or other enzymes, in active form, for topical application to the skin by consumers with or without professional supervision. The difficulty is that enzymes are labile and subject to denaturing by formulation temperatures or pH conditions, or by reaction with cosmetic vehicles during the extended periods of shelf storage that are normal in the cosmetic and pharmaceuticals manufacturing and distribution chains. Neither the liposomes described by Yarosh, nor the liposome gel would appear to offer sufficient protection to permit Yarosh or other enzymes to be formulated into consumer cosmetic products, such as creams, lotions or gels having adequate stability. The elevated processing temperatures, dispersing agents and extended shelf life required may decompose or denature not only the enzymes but their liposome carriers leading to unacceptable separation, loss of activity and the like.

There is accordingly a need for an esthetic cosmetic carrier for topically applied active agents that can protect labile actives such as botanical extracts, desquamating enzymes and the like, and deliver such agents to the slain in active form, while being suitable for formulation into traditional cosmetic vehicles. There are further needs for cosmetic or pharmaceutical delivery systems which offer separation of active from formulation ingredients and which can maintain that separation through typical formulation processes, especially those required for providing emulsions and for delivery systems which provide controlled release of actives at a delivery point and preferably also permit localized concentration of actives at the delivery point.

SUMMARY OF THE INVENTION

The invention, as claimed, is intended to provide a remedy for the problem of providing a delivery system for delivering labile and other actives to the skin, or other body surface, for topical application in a cosmetic or pharmaceutical formulation. It furthermore solves problems of delivering actives that may react undesirably with the delivery system itself, damaging the active or causing stability problems with the formulation.

Accordingly, the invention provides a protective cosmetic particulate gel delivery system for a topically applied active agent comprising discrete gel particles formed of:
  a) an agar gel; and
  b) a restraining polymer dispersed in the agar gel, the restraining polymer having sufficient molecular weight to prevent egress of the restraining polymer from the agar gel, having retention groups to bind the active agent to the restraining polymer for retention in the gel particles and being present in a proportion sufficient to deliver an effective amount of the active agent;
wherein the gel particles are manually crushable on the skin to increase the surface area of the gel particle material and expose the restraining polymer to the skin or other body surface for release of the active agent.

Preferably, active agent molecules are bound to the restraining polymer retention groups and the restraining polymer has an average molecular weight of at least 100,000 daltons. In a preferred embodiment, the active agent and the retention groups both comprise polar groups and are of opposite polarity whereby the active agent can bind ionically with the retention groups. A suitable restraining polymer is water-soluble and has a polysaccharide backbone substituted with strongly cationic quaternary ammonium groups which can act as retention groups for a range of active agents. The cationic ammonium groups are able to form stable ionic bonds with anionic actives which bonds can be broken to release the active upon topical application of the containing cosmetic composition.

Some suitable ionically bondable active agents are antioxidants, e.g. vitamin C (ascorbic acid), botanically derived polyphenols, procyanidin oligomers, free radical scavengers, and topically active enzymes. Desired nonionic actives, for example vitamin E (alpha-tocopherol), can bind to lipid groups on preferred restraining polymers, by hydrophobic interaction. While agar is a particularly preferred gel-forming agent, other gel-forming agents that meet the requirements of the invention can be used.

The invention thus provides a delivery system for delivering actives to the skin wherein one or more active agents is entrapped within a complexed-agar bead containing, in addition to agar, a restraining polymer to which the active bonds and from which it is not released until it reaches a target environment. The agar complex beads can be formed in various sizes to deliver actives, including pharmaceutical drugs or even biological cells, to the skin and applied to the skin as soft crushable beads.

Many desired active materials entrapped in an agar gel, leach out over time, especially if stored in an aqueous vehicle. In contrast, the restraining polymer has a molecular weight sufficient, for example 100,000 daltons or more, to prevent it from being released out of the agar matrix, so that, being bound to the polymer, the active is not released from the agar bead. The agar beads formed are preferably soft enough to be crushed on the skin during normal application of a cosmetic formulation.

The invention also provides a method of preparing agar-polymer complex gel particles comprising the steps of:
  a) dissolving agar and a water-soluble restraining polymer in water heated to an elevated temperature sufficient to dissolve the agar, in a proportion of agar to water effective to form a gel at lower temperatures;

b) cooling the hot agar solution to an intermediate temperature above the gelling point of the agar solution; and c) discharging the cooled agar-polymer solution through a needle to form drops; and d) exposing the drops to a hydrophobic liquid maintained at a temperature below the agar gelling point;

whereby the drops are formed into gel beads incorporating the restraining polymer. An active agent can be admixed in step a) or, if temperature-sensitive, in step b) whereby the active agent is incorporated in the gel beads.

While reference is made herein to the skin as a delivery target for active agents, it will be appreciated that the nails, hair, mouth, teeth wound tissue, or other accessible endogenous body surfaces can be similarly targeted, depending upon the active and the cosmetic or medicament vehicle into which the beads are formulated.

BRIEF DESCRIPTION OF THE DRAWINGS

Some illustrative embodiments of the invention, and the best mode contemplated of carrying out the invention, are described in detail below with reference to the accompanying drawings in which.

DETAILED DESCRIPTION OF THE PREFERRED EMBODIMENTS

All parts and proportions referenced in this description, unless otherwise stated, are on a weight or weight-for-weight basis.

Figure 1:
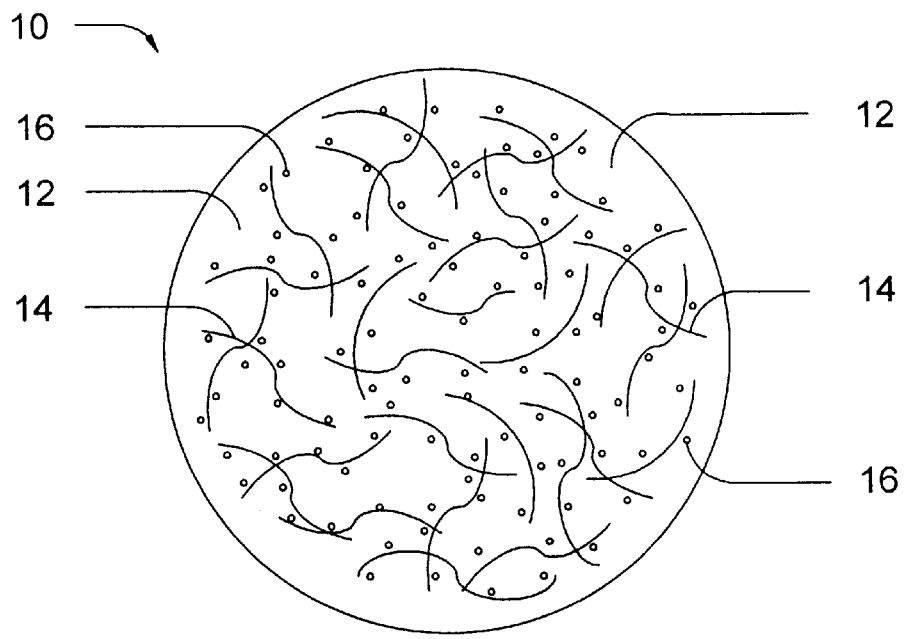
FIG. 1 is a schematic view of an embodiment of cosmetic gel particle carrier according to the invention which takes the form of an agar bead.
Figure 2:
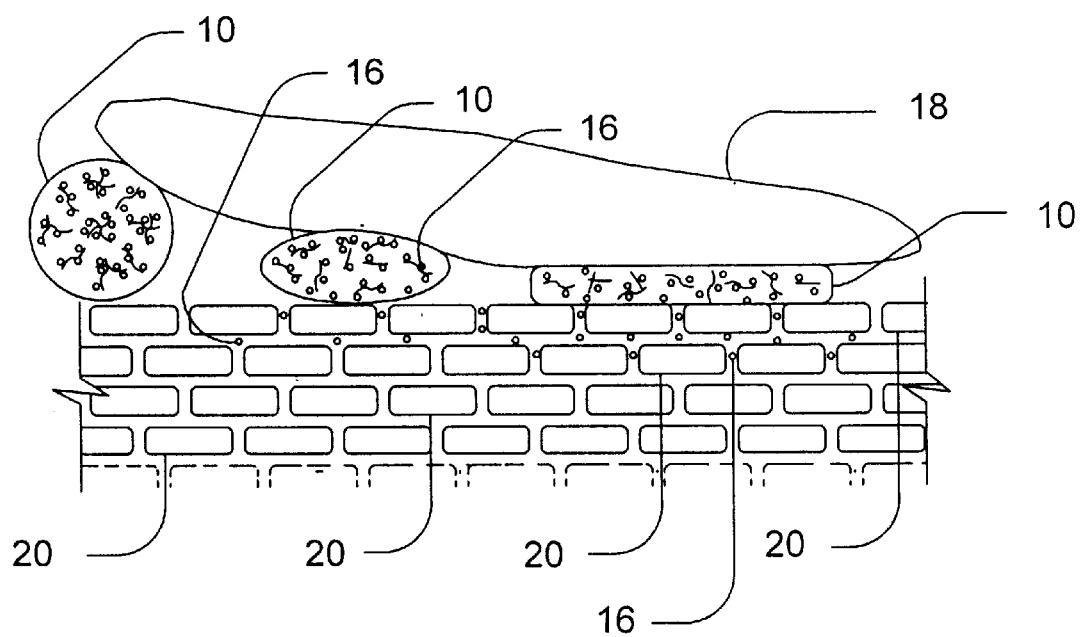
FIG. 2 is a schematic view showing several of the agar beads shown in FIG. 1 being crushed on the skin of a user.

Referring to FIGS. 1 and 2, a particularly preferred embodiment of particulate cosmetic gel carrier comprises relatively small agar particles or agar beads 10 having an average particle size measured in millimeters. The particles are small enough for cosmetic use, and preferably do not exceed 10 mm. in diameter, on average, but not so small as to penetrate the skin or skin pores. A minimum diameter, on average, is about 0.05 mm. (50 microns). A preferred range of particle sizes is from about 0.1 to 3.0 mm. in diameter, on average, with a more preferred range being from about 0.25 mm. to about 1 mm. in diameter, on average.

Preferred methods of producing the particles yield a well-focussed size distribution, so that it is preferred that at least 80 percent of the particles, more preferably 90 percent of the particles, lie within a desired average particle size bracket extending up to about 30 percent either side of a targeted average. If desired, for particular applications, a more uniform product can be obtained by mesh filtration.

Agar beads 10 are complexes of a continuous phase of agar gel 12 in a self-supporting solid or semi-solid form with a restraining polymer 14. Dispersed randomly throughout each agar bead 10 is a water-soluble, preferably polar, restraining polymer 14, preferably a quaternized cationic polymer, such as polyquaternium 24 or steardimonium hydroxyethylcellulose. Restraining polymer 14 is entrapped in agar gel 12 so that it is not readily leached or otherwise released therefrom so long as the bead 10 retains its integrity. Agar beads 10 can serve as a cosmetic delivery system for various active agents 16 which are bound to restraining polymer 14, for example ascorbic acid, lactic acid or papain, or alternatively they may be useful in their own right, without any further active ingredient, for example to deliver an entrapped restraining polymer, such as hyaluronic acid, a moisturizer, which has cosmetic or other active properties of its own. There are numerous possible alternative substances or materials to the preferred embodiments stated for agar gel 12, restraining polymer 14, and active agent 16, some of which are set forth hereinbelow. Others will be apparent to those skilled in the art.

As suggested schematically in FIG. 2, agar beads 10 can be manually crushed on the skin, preferably by an ordinary spreading or massaging action of one or more of the user's fingers 18, (or hands or equivalent other body parts, or implements), increasing the surface area of the agar beads 10 and bringing restraining polymer 14 into contact with the surface of the skin where normal skin constituents can release the active agent 10 from the restraining polymer 14, permitting it to permeate into the outer layers of stratum corneum skin cells 20. In FIG. 2, skin cells 20 have been exaggerated in size for clarity.

Continued spreading and massaging by the user's fingers 18 spreads the agar gel complex, with restraining polymer 14, over the skin surface where it can exercise its active properties, such as moisturizing, if it has any. Alternatively, if the polymer is substantially inert, along with the agar gel itself, the polymer will suffer one of the usual fates of cosmetic residues of being rubbed or washed off the skin or of being absorbed and enzymatically degraded or ultimately, if sufficiently inert, excreted.

Several different physico-chemical mechanisms of action are available to release active agents 16 from the restraining polymer 14 when the polymer 14 is exposed to the skin environment by crushing and spreading the agar beads. Sweat and sebum glands constantly discharge, respectively, moisture laden with various ionics, notably sodium chloride, at low strength, and a mix of lipids with phospholipids. The agar-polymer complex beads 10 of the invention are sufficiently large that they do not penetrate normal skin pores, follicular openings and the like. As the agar bead material is crushed and spread on the skin, its surface area increases providing an extended interface between the gel-polymer complex and any superficial skin moisture or lipids, initiating gradual release of active agent 16.

The ionic strength of skin moisture can break ionic bonds with the restraining polymer 14, encouraging migration of ionic active agents 16 to moist areas of the skin. Alternatively, the normal acidity of the skin, pH about 5.5, may release cationic actives 16 bound ionically to restraining polymer 14. In addition, natural skin lipids, such as sebum, may release lipophilically bound active agents.

If the skin is dry, with time, the gel-polymer complex can permeate through the skin moisture barrier constituted by the outermost keratinous layers of stratum corneum cells 20, and by the lipophilic "mortar" in the intercellular spaces 22, that bind cells 20 together, they encounter moisture and lipids to release actives. Such action may be encouraged by enzymatic lysing of the gel or polymer. The scope of the invention is not limited by the foregoing, or any other, theories or contemplated mechanism of action, which are provided by way of explanation, but only by the appended claims. What is significant is that the invention provides a delivery system which can successfully deliver actives to the skin surface and, if desired, protect those actives in cosmetic or other vehicles, during formulation or on the shelf, or both.

Some substances and materials usable in the practice of the invention are described in the following paragraphs. Others will be apparent to those skilled in the art.

Gel-forming agents: A particularly preferred gel-forming agent for use in the practice of the invention is agar, also known as "agar-agar". More properly referenced "agarose," which is the neutral gelling fraction of agar (the other being a sulfated non-gelling fraction "agaropectin"), the term "agar" is nevertheless used herein in the same sense as "agarose". Agar is an example of a gel-forming polysaccharide commonly used as a medium for electrophoresis and chromatography. Agar is insoluble when dispersed as a dry solid in water at low temperatures, however, it becomes soluble when heated to temperatures over 70–90° C. and forms a gel upon cooling. Agar is relatively expensive in comparison with some other commonly used gelling agents, but is particularly well suited for formulation with cosmetic vehicles, especially two-phase creams, gels and lotions which are usually homogenized at an elevated temperature. Agar gels are stable to both pH and moderate elevation of temperature. Surprisingly, preferred embodiments of agar-polymer complex gel beads can be formulated into cosmetic creams, employing aqueous phase ingredients and temperatures as high as 80° C., without losing their integrity, and while continuing to protect contained actives. Agar gel beads are stable, once formed, and are difficult to solublize in aqueous media, even at elevated temperatures. The beads of the invention are thus sufficiently durable to remain stable for the relatively short period at elevated temperature, e.g. up to about 10 minutes, required for homogenization of cream or other emulsions, and in fact should be stable for up to about 30 or 40 minutes. In addition, ungelled agar solutions are stable at temperatures as high as 100° C., which is advantageous for solids loading, permitting high concentrations of active and restraining polymer to be dissolved.

However, in preparing the agar-gel beads or formulating them into cosmetics, care should be talken to avoid exposing heat-sensitive agents to excessive heat, by adding them at lower temperatures, adding beads to cosmetic formulations after emulsification or by exposing beads containing such heat-sensitive actives for only short periods of time insufficient to be damaging.

While agar is a particularly preferred gel for use in the practice of the invention, other gels meeting the requirements of the invention can be used. Such other gels should be capable of forming dimensionally stable, self-supporting gel-polymer complex particles that are stable under the conditions of formulation, if any, (the particles themselves may constitute the end product), packaging and storage, and which can be crushed, spread or otherwise dispersed on the skin or nails of an end user to increase the surface area of the particles and disperse contained active in situ. The beads are preferably not unduly tacky and do not adhere to one another on contact. Preferred gels are water-soluble polymers that are pH stable. Preferably also, they should be such as can yield polymer-complex beads that are stable, when exposed with mixing, to an aqueous environment at about 50° C. for at least 5 and preferably 15 minutes. Still more preferably, the polymer complex beads produced should be stable, when exposed with mixing, to an aqueous environment at about 80° C., for at least 5, and preferably 15, minutes.

Other such possible gels will be known or apparent to those skilled in the art, in the light of the disclosure herein, and may include: synthetic polymers, such as vinyl or acrylamide polymers, or copolymers; natural polymers, for example polysaccharides, or proteins or synthetically modified ones of such polymers; botanically derived gels; and may include gelling agents such as carbopol, a common, low-cost petroleum-derived, cosmetic gel. However carbopol's gelling characteristics depend on pH levels, so that it not a suitable protectant for many actives for example alpha hydroxy acids.

It will be understood that the gel-forming agent selected for use in the practice of the invention should not only satisfy the particle or bead forming requirements described herein, but should also meet any requirements associated with the intended cosmetic, pharmaceutical, medicament, or other end use of the bead. Some other such gel-forming polymers are disclosed in Cini et al., supra, see for example, column 4, line 11 to column 6, line 30, the disclosure of which is hereby incorporated herein by reference thereto.

Restraining polymer. As stated above, the restraining polymer employed in practicing the invention has sufficient molecular weight to prevent egress of the restraining polymer from the agar gel, and has retention groups to bind the active agent to the restraining polymer for retention in the gel particles. Preferably also, it is water-soluble to a sufficient extent that a desired proportion can be co-dissolved with agar in an initial particle-forming step. The restraining polymer used is preferably selected according to the desired active agent or agents to have one or more retention groups which will bind the active agent.

Pursuant to the invention, it has been discovered that polymers with an average molecular weight of about 100,000 daltons, and more, are unable to flow through a preferred agar gel matrix. However, certain polymers, especially polymers capable of interacting with the agar, may be adequately retained in an agar gel, for the purposes of the invention even although they have a lower average molecular weight, e.g down to 75,000 daltons, or even as low as 50,000 daltons. There is no particular upper limit to the molecular weight of the restraining polymer, although it is contemplated that the average molecular weight will not exceed several million, e.g. 5 million daltons, but preferably does not exceed 1 million daltons. A preferred range for the average molecular weight is from 75,000 to 125,000 daltons.

Some specific restraining polymers preferred for the practice of the invention are certain commercially available quaternized polysaccharides, especially celluloses, rich in quaternary groups, notably polyquaternium 24 available under the trademark QUATRISOFT LM-200 (Union Carbide Corporation), and the CRODACEL Q (trademark) range of alkyl quaternary cellulose polymers (Croda, Inc.), notably laurdimonium hydroxyethylcellulose, sold under the trademark CRODACEL QL, cocodimonium hydroxyethylcellulose, sold under the trademark CRODACEL QM and steardimonium hydroxyethylcellulose, sold under the trademark CRODACEL QS. The CRODACEL Q (trademark) polymers belong to a class of polymers having repeating units of the following general nature:

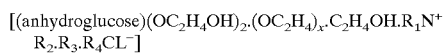

where x is often unspecified but may be taken to be under 10 and may be 0; $R_1$ is commonly methylene; $R_2$ and $R_3$ are frequently methyl and $R_4$ is the characteristic longer alkyl group, e.g. 10–30 carbon atoms such as lauryl, cocoyl or stearyl. The polyquatemium 24 polymers lack the two hydroxyethyl substituents. Each anhydroglucose unit can have a maximum of three ethoxy substituents, as shown, but in practice, the average degree of ethoxy substitution will be substantially lower so that the indication of di-hydroxyethyl substitution should be regarded as a theoretical limit rather than a practical representation. Thus, each repeating anhydroglucose or saccharide unit contains up to two hydroxyethyl substituents and a quaternary ammonium group attached to the polysaccharide nucleus via a short polyethoxy chain. Polyquatemium polymers lack the longer alkyl group and the lipophilic character it confers.

Of particular importance is the quaternary nitrogen atom which provides a cationic binding site for anionic actives. The $R_4$ allyl chain can provide a lipophilic anchor for lipid or lipophilic actives. the CRODACEL Q (trademark) range of quaternized celluloses are more fully described in a product data sheet entitled "*Crodarel Q range*" from Croda Chemicals Ltd., UK, the disclosure of which is hereby incorporated herein by reference thereto. They are supplied as somewhat hazy or opaque viscous concentrates intended for dilution and are known as film-forming agents with particular application in hair shampoos and conditioners, where their ability to be substantive to the hair, i.e. to attach themselves to the hair in a substantive manner, without creating build-up, is valuable. These and similar polymers suitable for use in the practice of this invention are well known in the literature and are described, for example, in U.S. Pat. Nos. 5,135,748 (Ziegler et al.), 4,970,067 (Panandilker et al.), 5,288,484 (Tashjian) the disclosures of which are also hereby incorporated herein by reference thereto.

Quantitatively, it is theoretically possible for each polar group to bind one acidic molecule of the entrapped active, assuming the active molecule is small enough to fit. In order to produce an end-user cosmetic suspension with a desirably high concentration of active, the ionic bonding capacity should be as high as practical and so must be the number of cationic groups bonded to the polymer backbone. While ratios as low as 0.2 or close to the theoretical limit of 2.0 may be useful, an average ratio of 0.5 moles to 1.5 moles of quaternary groups per glucose unit is preferred to provide a high loading capacity of the active to the agar bead without too high of a proportion of polymer to agar. In practice, a commercially available ratio of 1.2 moles of quaternary groups per glucose unit was used, this being the approximate number for steardimonium hydroxyethylcellulose, a strong anion exchanger, can be used, as well as, weak anion exchangers (tertiary amines) and cation exchangers, either strong (sulfonate or phosphate groups) or weak (carboxyl groups).

Other polysaccharide polymers which, when suitably modified, can be used include starch, cellulose, chitosan and karageenan. Other polymers can be used such as modified proteins, polypeptides of adequate molecular weight, or non-biological polymers (e.g. acrylates). Protein-based or biological polymers may bring allergenicity problems, depending upon their heterogenicity, and are accordingly not preferred for use in the practice of the invention. However, relatively homogenous polyamino acids, e.g. polylysine, have low immunogenicity and are more suitable for use as the restraining polymer of the invention. The amino acid monomer, e.g one or more of the amino acid elements of natural polypeptides, can be selected to provide a desired retention unit, having desired binding characteristics with a particular target active, as will be apparent to those skilled in the art. Thus, at suitable pH levels, the basic, distal amino groups of polylysine or polyarginine can provide cationic retention moieties for anionic actives, while the distal carboxyl moieties of polyaspartic acid or polyglutamic acid, can provide anionic retention moieties for cationic actives.

Other suitable restraining polymers which can meet the requirements of the invention will be known or apparent to those skilled in the art, based upon the teachings of the disclosure herein. Mixtures of different restraining polymers can also be used.

Actives: Some examples of classes of dermally active, or dermally effective substances having biological or cosmetic activity, which can be topically delivered employing the delivery systems of the invention include: antioxidants including botanically derived polyphenols, for example procyanidin oligomers; free radical scavengers; topically active enzymes, for example, antibacterials, such as glucose oxidase, antioxidants such as superoxide dismutase, and proteolytic enzymes such as bromelain and papain, (useful for enzyme peeling); other enzymes such as the DNA repair enzymes described above; exfoliative retinoids, such as retinol and retinol esters including retinol acetate, vitamin A palmitate; purified plant extracts and plant proteins; whitening agents such as arbutin; essential fatty acids, such as linoleic acid, linolenic acid and arachidonic acid; animal proteins, for example collagen, elastin and keratin; moisturizers, such as hyaluronic acid and other glycosaminoglycans; ultraviolet light filters; coated or uncoated organic and inorganic pigments such as titanium, zinc, and iron oxides; melanin or a sepia ink extract; other colorants or dyes, and perfumes. While pigments and perfumes may have a role in enhancing the esthetic appeal of the carrier gel beads in which they are incorporated, they may also perform cosmetic functions when the gel beads are applied to the skin or other endogenous surfaces, for example, the nails or hair and then crushed, commencing controlled release of the actives. The release can, to some extent, be user controllable. Thus, for example, a user may firmly spread a body cream containing perfume-loaded gel-complex beads according to the invention, until they detect enough perfume is released or a rouge, makeup, foundation or other pigmented cosmetic, until the color is to their liking. The carrier beads and the respective proportions of their components may be adjusted to provide continued release to sustain the color or perfume intensity. In addition, the user may, with small, hard-to-see beads, refresh the active by further crushing and spreading residual uncrushed gel beads, at a later time.

In general, any active can be used that binds satisfactorily to the restraining polymer and can be released by contact with the skin. Many novel formulations and enhancements of known cosmetics that can be obtained by supplementing them with labile actives carried within and protected by the polymer-gel complex beads of the invention, will be apparent to those skilled in the art. One such product comprises a mixture of actives providing a novel prophylactic and therapeutic treatment for solar exposure comprises an ultraviolet absorbent or screening agent, for example titanium dioxide, an antioxidant, for example vitamin E, and a DNA repair enzyme, incorporated into agar-polymer complex beads, according to the invention. If desired, a melanocyte stimulant could be included. Such beads could be used per se, or incorporated into traditional creams or lotions.

Preferred Actives: Some examples of particularly preferred actives for delivery by the gel carrier particles of the invention are: ascorbic acid (vitamin C), alpha-tocopherol (vitamin E), tocopherol acetate (vitamin E acetate), purified papain extract, beta-carotene, green tea extract rich in polyphenols, purified extracts of procyanidolic oligomers from grape seed or pine bark, monoazoic dye e.g. D&C orange, xanthenic dye (disodium salt), cinnamic acid and octylmethoxycinnamate.

Surprisingly, all of these materials can be effectively bound to a modified starch restraining polymer containing quaternary ammonium groups, incorporated in the protective gel carrier particles of the invention, and then formulated into a cosmetic cream so that they retain their activity, or cosmetic properties, when applied topically. Furthermore, multiple such actives can be similarly bound to a suitable restraining polymer and incorporated in protective gel carrier particles, to deliver their desired properties to end users in topical formulations, for example, an antioxidant combination of vitamins C and E, colored with three colorants, and one or more colorants combined with papain, or other such preferred active.

One preferred class of actives is anionic, a particularly preferred restraining polymer to which the actives bind being a modified polysaccharides containing quaternary ammonium groups which are cationic and are able to form stable ionic bonds with many anionic actives.

Water. Water is also a significant ingredient of the carrier particles of the invention, being the medium through which colloidal agar particles are dispersed to provide a semi-solid or nearly solid gel. Other aqueous media, or possibly, polar alcohols or glycols, may substitute for water. In preparing the agar beads of the invention, agar and other ingredients are mixed with water and injected through a needle as a warm solution or dispersion, at a speed controlled to generate drops, then cooled to set the gel.

Proportions. The proportion of solids to water should be sufficient to dissolve or disperse the solids and to ensure they will remain in solution or dispersed until desired gel formation in the oil medium, after the droplets leave the injection needle.

Preferably the solids comprise from about 0.5 to about 40 percent by weight of the solution or dispersion and more preferably from about 1.5 to about 25 percent by weight. The relative proportion of restraining polymer 14 to agar 12 can be as low as 1:10, but to obtain a satisfactory loading of active agent 16 (which can, in certain instances, be the polymer itself, e.g. hyaluronic acid) a proportion of at least 1:1, up to about 10:1 restraining polymer 14 to agar 12, is desirable. Preferably, a proportion of from about 2:1 to about 6:1 is used.

The proportion of active agent 16, assuming such to be additional to the restraining polymer 14, will usually be made as high as practical, without affecting the integrity of the particle or causing unacceptable instabilities in storage. The maximum practical loading of active, a desirable objective, will vary substantially, depending upon the nature of active agent 16 and will usually be related to the quantity of restraining polymer 14. Depending upon the potency of the active, and other factors such as its physical form, the proportion of active agent to restraining polymer may range from about 0.01:1 to about 10:1, preferably from about 0.1:1 to about 5.0:1. Preferably also, the active agent comprises from about 0.01 to about 20 percent of the solution, or dispersion, at the injection needle, more preferably about 0.1 to about 10 percent.

The foregoing relative proportions are, as previously stated, based on weight, and are also based on the ingredients of the solution or dispersion at the injection needle. With proper manufacturing or production procedures, these proportions should largely be reflected in the end product agar complex gel beads themselves, but variations may occur.

Cosmetic formulations. Cosmetic formulations, diluents or cosmetic vehicles are compositions applied externally to the skin, hair or nails for purposes of cleansing, beautifying, conditioning or protecting the body surface. Cosmetic formulations include but are not limited to water-in-oil or oil-in-water emulsions in cream or lotion form, sunscreens, toners, astringents, facial make-ups, powders, and skin cleansing compositions. The recipes for such compositions are well known to those skilled in the art and can be found in many publications in the field. A brief summary of some such cosmetic "diluents" that can be used in the practice of the invention appears in Wolf et al. U.S. Pat. No. 5,449,519, for example at column 4, line 25 to column 6, line 56, the disclosure of which is hereby incorporated herein by reference thereto. The gel-complex particles of the invention are generally suitable for incorporation into such cosmetic compositions or "diluents" and the invention extends to the resultant gel-complex particle containing compositions which have beneficial properties arising from the presence of the gel-complex particles, for example new active ingredients, new concentrations of active ingredients, or simply better delivery of active ingredients with reduced loss of activity.

The gel beads of the invention can be used in such cosmetic compositions in any desired concentration or proportion that will provide an effective amount of active agent upon application, for example from 0.1 to 90 percent by weight of the total composition, preferably from 1 to 50 percent, and more preferably from 5 to 25 percent by weight of the total composition.

Figure 3:
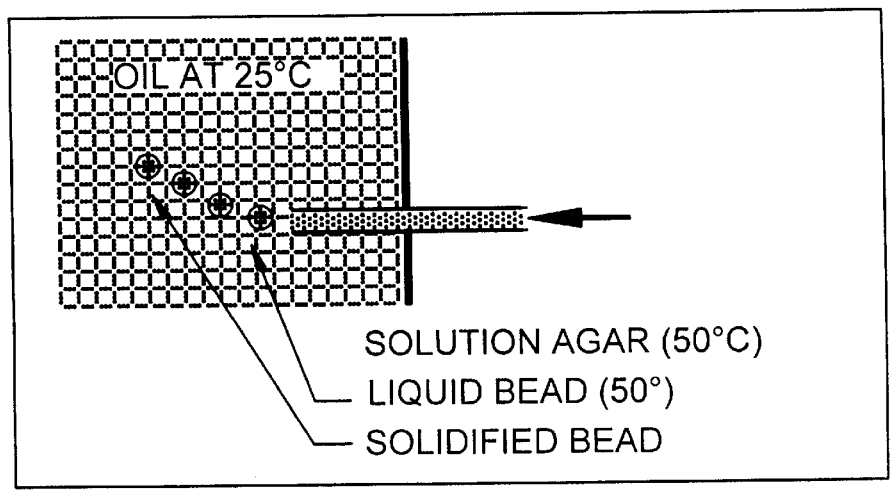
FIG. 3 is a schematic representation of a prior art process for making agar gel beads.

Manufacture. As shown in FIG. 3, it is known to make agar gel beads by dissolving granular agar in deionized or distilled water heated to an elevated temperature sufficient to dissolve the agar, using a proportion of agar to water effective to form a gel at lower temperatures, cooling the hot agar solution to a suitable intermediate temperature above the gelling point of the agar solution, typically about 30° C., and injecting the cooled solution through an injection needle, sized according to the desired agar bead size, into a hydrophobic liquid maintained at a temperature suitably below the agar gelling point for bead formation, at a rate of injection controlled to favor bead formation. As indicated in the illustrative example of FIG. 3, the dissolved agar is cooled to about 50° C. and injected into an oil medium, e.g. a paraffin bath, at about 2.5° C., whereupon the agar gel beads solidify as they leave the injection needle.

In the method of the invention, a suitable restraining polymer, and the active agent, if any, dissolved or dispersed in water or an aqueous solvent system, are mixed with the agar solution before injection into the hydrophobic liquid. Suitable restraining polymers, and many actives, are generally temperature stable and can be mixed with the agar granules and heated to the elevated temperature to provide a clear solution of all ingredients. Less stable actives, for example, enzymes, can be introduced to the agar-polymer solution at the intermediate temperature, preferably in aqueous solution or suspension.

The temperatures of both the agar mixture and the paraffin bath are chosen and adjusted according to the type of bead being produce, i.e. its constituents, toward the goal of providing separable, pourable beads which can be crushed or spread on the skin. In particular, they are adjusted to ensure that the viscosity of the hot agar mixture is low enough to permit the mixture to be pumped through the injection needle. The viscosity will vary with different bead formulations, being increased by higher concentrations of ionic actives.

Other methods of forming gelatinous beads will be known or apparent to those skilled in the art, and may be adapted to the purposes of the invention. For example, instead of injecting drops of warm agar solution into a cold oil bath, the warm solution may be dripped from above on to the surface of cold oily medium.

If desired the active agent and the restraining polymer can be premixed to foster bonding of the active to the restraining polymer, in a preliminary step. Lipophilic acids, can if desired, be bonded to the restraining polymer in a preliminary mixing step employing a lipophilic solvent which is evaporated or otherwise removed prior to mixing with the agar solution.

The resultant beads comprise a complex of active-loaded restraining polymer entrapped in an agar matrix. The beads are soft, clear, glossy, odor-free and esthetically appealing, pH-stable and temperature stable to temperatures up to about 80° C. The hardness, or preferably softness of the beads is preferably carefully chosen, by appropriate selection of processing parameters, according to the bead components, so that the beads are hard enough to be conveniently handled, transferred from drums to formulation vessels, and the like, and hard enough to resist breakdown in mixers or homogenizers, yet soft enough to be crushed on the skin, and preferably sufficiently soft to be spread and "disappear".

A principal parameter affecting the hardness is the agar concentration (higher concentrations form harder beads), but oily actives will soften the beads and the concentration and composition of the restraining polymer can also affect the hardnes of the bead. These parameters are preferably selected and controlled to provide the desired hardness, which is that of a soft, pleasant crushable feel.

Figure 4:
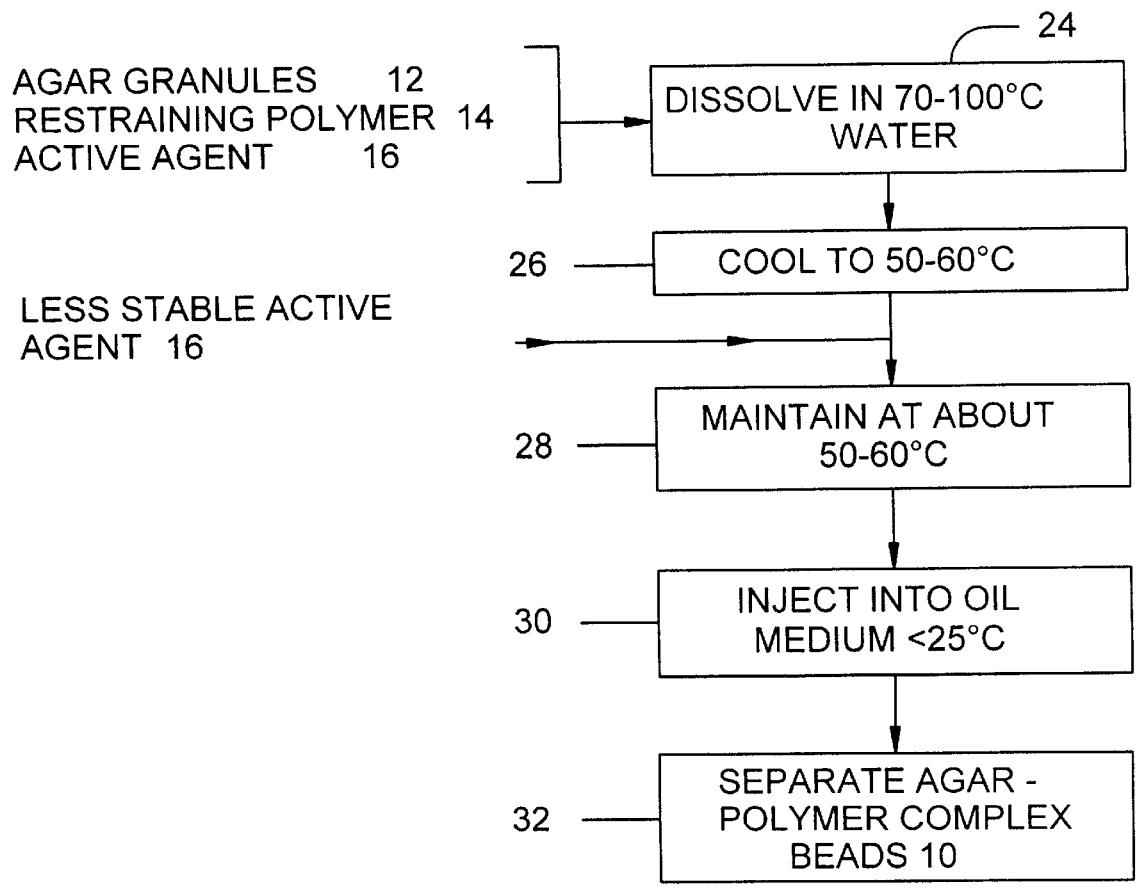
FIG. 4 is a block flow diagram of an embodiment of a method of manufacturing agar-polymer complex beads according to the invention.

Referring to the manufacturing process illustrated schematically in FIG. 4, agar granules 12, restraining polymer 14 and stable active agent 16, if used, are dissolved and, if appropriate, dispersed, in a mixing step 24 in deionized or distilled water, conducted at an elevated temperature, preferably between about 70 and about 100° C., more preferably between about 85 and about 95° C., or about 90° C. Upon heating, the suspension becomes a clear solution.

The solution or dispersion is cooled in a cooling step 26 to an intermediate temperature above the gelling point of the solution or dispersion where less heat must be lost from the solution or dispersion to precipitate gelation. The intermediate temperature may range from about 40 to about 70° C., preferably from about 50 to about 60° C. Less stable actives, for example enzymes, dissolved or dispersed in water are incorporated in, and mixed with, the agar-polymer solution at the intermediate temperature to avoid detrimental effects of the higher temperature. Enzyme-containing solutions should be kept near to about 50° C. to avoid denaturing which may occur at temperatures around 60° C.

Optionally the solution is temperature stabilized, at the intermediate temperature, for example, using a water jacket or bath, maintained at a temperature of about 50° C., in temperature-stabilization step 28.

The liquid solution or dispersion is then pumped through a needle submerged in a liquid paraffin oil bath maintained at a temperature below the gelling point of the solution or dispersion, namely below about 30° C., preferably below about 25° C., more preferably about 0 to 10° C., while mixing, in oil injection step 30. Because water and oil are immiscible, the pumped solution of warm agar, polymer and active, form droplets when extruded into the oil. The low temperature of the oil "freezes" the droplets in shape, causing the agar medium to gel into agar-polymer complex beads 10.

The agar-polymer complex beads 10 are separated, washed to remove the paraffin oil, filtered and dried, in separation step 32.

Large gel particles, up to approximately 2 mm in diameter, can be colored, filled with actives and formulated in a transparent gel, the colorants and actives being incorporated in the injection solution or dispersion. Different sized beads can be produced by adjusting the size of the needle diameter or the agitation speed of the oil bath, higher speeds producing smaller beads.

Some non-limiting examples of the practice of the invention will now be described by way of illustration.

EXAMPLE 1

Preparation of Agar Complex Beads using Polyquaternium 24

1.5 g of agar granules (OSI-France) with a gelling point of about 33° C. and 1.5 g of polyquaternium 24 [QUATRISOFT LM-200 trademark Union Carbide Corporation (Amerchol-France)] are mixed in 97 g of distilled water and heated to 90° C. The suspension becomes a clear solution at this temperature and it is then allowed to cool to 50° C. in a water bath. The solution is then pumped through a needle by means of a peristaltic pump (Bioblock-France) and the needle is placed into a liquid paraffin oil bath maintained at 5° C. while mixing (250 rpm). The pump flow rate is adjusted to 2.5 ml/minute and the liquid is injected into the oil bath. Gel beads are formed in the oil phase and their size depends upon the inner diameter of the needle. For this example, two different sized needles were used: 0.45×12 mm or 0.8×50 mm (inner diameter×length). The gel beads are separated by filtration on a 0.2 mm screen and extensively washed with water. In this example, 2 mm diameter beads are typically formed. Smaller beads are formed using higher mixing rates (e.g. 1200 rpm) while smaller needle diameters help maintain small diameter. The gel beads formed are smooth, shiny and soft. Surprisingly, the presence of the restraining polymer does not significantly alter the ability of the agar to gel and form stable beads when cooled in oil.

EXAMPLE 2

Preparation of Agar Complex Beads using Hyaluronic Acid as Anionic Copolymer

The procedure of Example 1 is followed except hyaluronic acid (Soliance-France) is mixed with the agar instead of polyquaternium 24. The beads formed by this procedure are suitable for use either as a moisturizer, delivering hyaluronic acid, or as a delivery system for cationic actives attached or bound to the hyaluronic acid.

EXAMPLE 3

Preparation of Agar Complex Beads using Steardimonium Hydroxyethylcellulose

The same procedure as in Example 1 is used, except that 7.5 g of steardimonium hydroxyethylcellulose (CRODACEL QS, trademark, Croda, Inc.) is substituted for the polyquaternium 24. Similar beads are obtained after extrusion into a 5° C. oil bath.

EXAMPLE 4

Preparation of Agar Complex Beads Containing an Enzyme, Papain 1.5 g of agar and 7.5 g of steardimonium hydroxyethylcellulose are mixed in 56 g of distilled water and heated to 90° C. under mixing to obtain a clear solution. The mixture is allowed to cool at 60° C. and 5 g of papain in 30 g of distilled water is added to the solution. The mixture is maintained at 50° C. in a water bath, then injected into liquid parafin oil at 5° C. under mixing (250 rpm). 2 mm diameter beads are formed, separated and washed with water.

EXAMPLE 5

Preparation of Agar Complex Beads Containing a Colorant

Following the procedure of previous examples, 1.5 g of agar, 7.5 g of steardimonium hydroxyethylcellulose and 0.5 g of FDC Blue (Colorants Wackherr-France) are dispersed together in 90.5 g of distilled water. The 2 mm diameter beads are formed in the oil bath, then separated and washed with water.

EXAMPLE 6

Preparation of Agar Complex Beads Containing a Plant Extract

Following the procedure of previous examples, 0.6 g of agar, 0.2 g of steardimonium hydroxyethylcellulose (trademark), 1.0 g of polyquaternium 24 and 1.0 g of green tea extract (Rahn AG Switzerland) are dispersed in 30 g of distilled water and heated to 90° C. under mixing. 2 mm diameter beads are formed in the oil, then separated and washed with water.

EXAMPLE 7

Preparation of Agar Complex Beads Containing a Lipophilic Active, Beta-Carotene 1.5 g of agar is dispersed in 70.5 g of water and heated to 90° C. under mixing to obtain a clear solution which is allowed to cool at 60° C. Then 7.5 g steardimonium hydroxyethylcellulose and 0.5 g of β-carotene (Cooperation Pharmaceutique Francaise-France) predispersed in oil, is dispersed in 20 g of distilled water and mixed with the above solution. The restraining polymer facilitates dispersion of the hydrophobic β-carotene. The mixture is maintained at 50° C. and injected through a needle (0.45×12 mm) into liquid parafin oil at 5° C. under mixing. The beads produced containing the β-carotene have an average diameter of 2 mm.

EXAMPLE 8

Preparation of Agar Complex Beads Containing both Hydrophilic and Lipophilic Actives: Vitamin C and Vitamin E Following the procedure of Example 7, 1.5 g of agar, 7.5 g of steardimonium hydroxyethylcellulose, 7.5 g of ascorbic acid (Cooperation Pharmaceutique Francaise-France), 2.5 g of α-tocopherol (Fluka-Switzerland) are mixed in 81 g of distilled water. 2 mm diameter beads containing vitamins C and E are obtained in the oil phase, then separated and washed with water.

EXAMPLE 9

Preparation of Agar Complex Beads Containing a Pigment

Following the procedure of Example 7, 1.5 g of agar, 1.5 g of steardimonium hydroxyethylcellulose, 5 g of titanium dioxide (ADF Chimie-France) and 2.5 g of iron oxide (Kobo Products USA) are mixed in 89.5 g of distilled water. 2 mm diameter beads containing the pigment are formed in the oil phase, then separated and washed with water.

EXAMPLE 10

Modification of the Preparation Method for Agar Complex Beads

Following the procedure of the previous Examples, a clear agar solution with various additional ingredients, as recited, is maintained at 50° C., then pumped through a needle. However, in this example, the needle is placed 10 cm above the surface of the paraffin oil bath. Individual droplets are formed in air and fall into the cooled liquid, generating beads. The beads have the same appearance as the above described beads but their average size also depends upon the agitation speed of the oil bath. 0.5 mm to 2 mm diameter beads can be generated using the same type of needle with speed rates ranging from 100 rpm to 250 rpm. The gel beads formed are smooth, soft and shiny.

ACTIVITY TEST

Activity of Ascorbic Acid after Entrapment within Agar Complex Beads

To determine if an active remains stable after its entrapment within mixed-agar beads, the activity of the ascorbic acid is measured by a DPPH test. In this test, 2,2 diphenyl-1-picrylhydrazyl (DPPH), a stable free-radical that exhibits an absorption band at 515 nm (violet color) which disappears upon reduction by an anti-free-radical agent.

Ascorbic acid is entrapped within the mixed-agar beads as set forth in the procedure in Example 8. Three 2 mm diameter beads containing an average ascorbic acid content of 2.25 mg and weighing approximately 30 mg each, were added to 3.5 ml of methanolic DPPH solution (DPPH concentration $0.6 \times 10^{-5}$ mol).

The beads were crushed in the test tube and the violet coloration attached to the DPPH disappeared within a few seconds. The experiment demonstrated that ascorbic acid entrapped in a complexed agar beads according to the invention retains its free radical scavenging activity.

While reference has been made to topical application of compositions containing the novel gel particle delivery systems of the invention, it will be understood that certain such gel delivery systems can, with benefit, be applied to tissues, e.g. wound tissue, and to other environments where the controllable release protection of actives, especially actives dispersed in an excipient, is important and where release of bound actives can be readily initiated.

INDUSTRIAL APPLICABILITY

The present invention is particularly suitable for application in the cosmetic industry providing novel consumer cosmetic products, for example, creams, gels and lotions containing gel-complex beads and the gel-complex beads themselves.

While some illustrative embodiments of the invention have been described above, it is, of course, understood that various modifications and equivalents of the described embodiments will be apparent to those of ordinary skill in the art. Some equivalents will be readily recognized by those of ordinary skill while others may require no more than routine experimentation. Such modifications and equivalents are within the spirit and scope of the invention, which is limited and defined only by the appended claims.

We claim:

1. A protective topical cosmetic particulate gel delivery system for a topically applied active agent comprising discrete gel particles having an average particle diameter of from about 0.05 mm to 10 mm and formed of:
   a) an agar gel; and
   b) a restraining polymer dispersed in the agar gel, the restraining polymer having a molecular weight of at least 50,000 daltons and effective to prevent egress of the restraining polymer from the agar gel, having retention groups to bind the active agent to the restraining polymer for retention in the gel particles, being present in a proportion effective to deliver an effective amount of the active agent and being selected from the group consisting of polyquaternium 24, laurdimonium hydroxyethylcellulose, cocodimonium hydroxyethylcellulose, steardimonium hydroxyethylcellulose, quaternary ammonium substituted water-soluble polysaccharides, alkyl quaternary celluloses and polypeptides having or provided with retention groups to retain the active agent;
   wherein the gel particles are manually crushable on the skin to increase the surface area of the gel particles and expose the restraining polymer to a topical body surface for release of the active agent.

2. A cosmetic particulate gel delivery system according to claim 1 further comprising active agent molecules bound to the restraining polymer retention groups wherein the restraining polymer has an average molecular weight of at least 100,000 daltons.

3. A cosmetic particulate gel delivery system according to claim 2 wherein the active agent and the retention groups both comprise polar groups and are of opposite polarity whereby the active agent can bind ionically with the retention groups.

4. A cosmetic particulate gel delivery system according to claim 1 wherein the active agent and the retention groups both comprise lipophilic groups whereby the active agent can bind lipophilically to the retention groups.

5. A cosmetic particulate gel delivery system according to claim 1 wherein the active agent is selected from the group consisting of antioxidants, botanically derived polyphenols, procyanidin oligomers, free radical scavengers, topically active enzymes, antibacterials, glucose oxidase, antioxidants, superoxide dismutase, proteolytic enzymes, bromelain, DNA repair enzymes, exfoliative retinoids, retinol, retinol esters, retinol acetate, vitamin A palmitate, purified plant extracts, plant proteins, whitening agents, arbutin, essential fatty acids, linoleic acid, linolenic acid, arachidonic acid, collagen, elastin, keratin, moisturizers, hyaluronic acid, glycosaminoglycans, ultraviolet light filters, ultraviolet light absorbents, coated and uncoated organic and inorganic pigments, titanium, zinc, and iron oxides, melanin, sepia ink extract, colorants, dyes and perfumes.

6. A method of preparing agar-polymer complex gel particles for topical delivery of an active agent, the gel particles having an average particle diameter of from about 0.05 mm to 10 mm, the method comprising the steps of:
   a) dissolving agar and a water-soluble restraining polymer in water heated to an elevated temperature effective to dissolve the agar, in a proportion of agar to water effective to form a gel at a lower temperature than the elevated temperature, the restraining polymer having a molecular weight of at least 50,000 daltons and effective to prevent egress of the restraining polymer from the agar gel when formed and being selected from the group consisting of polyquaternium 24, laurdimonium hydroxyethylcellulose, cocodimonium hydroxyethylcellulose, steardimonium hydroxyethylcellulose, quaternary ammonium substituted water-soluble polysaccharides, alkyl quaternary celluloses and polypeptides having or provided with retention groups to retain the active agent;
   b) cooling the hot agar solution to an intermediate temperature above the gelling point of the agar solution; and
   c) discharging the cooled agar-polymer solution through a needle to form drops; and
   d) exposing the drops to a hydrophobic liquid maintained at a temperature below the agar gelling point;
   whereby the drops are formed into gel beads incorporating the restraining polymer.

7. A method according to claim 6 comprising admixing an active agent in step a) whereby the active agent is incorporated in the gel beads.

8. A method according to claim 6 wherein the active agent is temperature sensitive, the method comprising admixing the temperature-sensitive active agent in step b) whereby the active agent is incorporated in the gel beads.

9. A cosmetic particulate gel delivery system according to claim 1 wherein the active agent comprises an effective quantity of a DNA repair enzyme incorporated in the gel beads in combination with a cosmetic vehicle whereby the combination is a sunscreen composition.

10. A sunscreen composition according to claim 9 further comprising an ultraviolet filtering material and a free radical scavenger.

11. A protective cosmetic particulate gel delivery system for a topically applied active agent, the delivery system comprising discrete, self-supporting gel particles of from 50 microns to 10 mm average size, the particles being insoluble in water at 25° C. and being formed of:
   a) an agar gel; and
   b) a restraining polymer, being a water-soluble polymer comprising a polysaccharide backbone substituted with cationic quaternary ammonium groups effectively charged to form stable ionic bonds with anionic actives, dispersed in the agar gel, the restraining polymer having an average molecular weight of at least 100,000 daltons, having retention groups to bind the active agent to the restraining polymer for retention in the gel particles, being present in a proportion effective to deliver an effective amount of the active agent and being selected from the group consisting of polyquaternium 24, laurdimonium hydroxyethylcellulose, cocodimonium hydroxyethylcellulose, steardimonium hydroxyethylcellulose, quaternary ammonium substituted water-soluble polysaccharides and allyl quaternary celluloses,
   wherein the gel particles are manually crushable on the skin to increase the surface area of the gel particles and expose the restraining polymer to a topical body surface for release of the active agent.

12. A sunscreen composition according to claim 10 wherein the ultraviolet filtering material comprises finely divided titanium dioxide or zinc oxide and the free radical scavenger comprises vitamin E.

13. A cosmetic particulate gel delivery system according to claim 1 wherein the particles have an average particle size in the range of from about 0.1 to about 3.0 mm.

14. A cosmetic particulate gel delivery system according to claim 13 wherein the particles have an average particle size in the range of from about 0.25 to about 1.0 mm.

* * * * *